United States Patent
Chiu et al.

(10) Patent No.: US 8,101,409 B2
(45) Date of Patent: Jan. 24, 2012

(54) ULTRA-NANOCRYSTALLINE DIAMOND AS A BIOMATERIAL FOR ENHANCING PROLIFERATION AND DIFFERENTIATION OF NEURAL STEM CELLS

(75) Inventors: Ing-Ming Chiu, Miaoli County (TW);
Ying-Chieh Chen, Miaoli County (TW);
Don-Ching Lee, Miaoli County (TW);
Nyan-Hwa Tai, Hsinchu (TW)

(73) Assignees: National Health Research Institutes, Miaoli County (TW); National Tsing Hua University, Hsinchu (TW)

( * ) Notice: Subject to any disclaimer, the term of this patent is extended or adjusted under 35 U.S.C. 154(b) by 148 days.

(21) Appl. No.: 12/573,878

(22) Filed: Oct. 5, 2009

(65) Prior Publication Data

US 2011/0081395 A1 Apr. 7, 2011

(51) Int. Cl.
*C12N 5/07* (2010.01)
*C12N 5/071* (2010.01)
*C12N 5/00* (2010.01)
*C12N 5/079* (2010.01)
*C12N 5/0793* (2010.01)
*C12N 5/0735* (2010.01)
*C12N 5/074* (2010.01)
*C12N 5/095* (2010.01)
*C12N 5/02* (2010.01)
*C12N 5/073* (2010.01)
*G01N 33/567* (2006.01)
*C03C 17/00* (2006.01)

(52) U.S. Cl. ....... 435/368; 435/366; 435/326; 435/7.21; 435/1.1; 435/384; 435/383; 65/33.4; 428/835; 428/833.2

(58) Field of Classification Search ................... None
See application file for complete search history.

(56) References Cited

OTHER PUBLICATIONS

Lechleitner et al., Biomaterials. 2008, 29: 4275-4284.*
Chong et al., Langmuir 2007. 23: 5615-5621.*
Kloss, F. R. et al. (2008) "The role of oxygen termination of nanocrystalline diamond on immobilisation of BMP-2 and subsequent bone formation." Biomaterials 29:2433-42.
Chen, Y. C. et al. (2009) "The effect of ultra-nanocrystalline diamond films on the proliferation and differentiation of neural stern cell." Biomaterials 30:2428-35.

* cited by examiner

*Primary Examiner* — Chang-Yu Wang
(74) *Attorney, Agent, or Firm* — Hsin-Ming Saunders; Intellectual Property Connections, Inc.

(57) ABSTRACT

Compositions for promoting growth and/or differentiation of a stem cell are disclosed. The composition comprises: a) a diamond film; b) a stem cell cultured on the diamond film; and c) a medium bathing the stem cell. The stem cell may be a mammalian neural stem cell and the diamond film may comprise a hydrogen-terminated or an oxygen-terminated surface. The hydrogen-terminated surface promotes proliferation and differentiation of a neural stem cell into neurons, and the oxygen-terminated surface promotes a neural stem cell to proliferate and differentiate into oligodendrocytes.

20 Claims, 5 Drawing Sheets

SEQUENCE LISTING

<160> NUMBER OF SEQ ID NOS: 16

<210> SEQ ID NO 1
<211> LENGTH: 19
<212> TYPE: DNA
<213> ORGANISM: Artificial Sequence
<220> FEATURE:
<223> OTHER INFORMATION: Sox2-F1

<400> SEQUENCE: 1
agaaccccaa gatgcacaa                                                    19

<210> SEQ ID NO 2
<211> LENGTH: 20
<212> TYPE: DNA
<213> ORGANISM: Artificial Sequence
<220> FEATURE:
<223> OTHER INFORMATION: Sox2-R2

<400> SEQUENCE: 2
atgtaggtct gcgagctggt                                                   20

<210> SEQ ID NO 3
<211> LENGTH: 20
<212> TYPE: DNA
<213> ORGANISM: Artificial Sequence
<220> FEATURE:
<223> OTHER INFORMATION: Sox1-F3

<400> SEQUENCE: 3
cacagcacta ccagggcgcg                                                   20

<210> SEQ ID NO 4
<211> LENGTH: 18
<212> TYPE: DNA
<213> ORGANISM: Artificial Sequence
<220> FEATURE:
<223> OTHER INFORMATION: Sox1-R4

<400> SEQUENCE: 4
cacctctgag aggggatt                                                     18

<210> SEQ ID NO 5
<211> LENGTH: 23
<212> TYPE: DNA
<213> ORGANISM: Artificial Sequence
<220> FEATURE:
<223> OTHER INFORMATION: CD133-F5

<400> SEQUENCE: 5
ttgcctgaag gaaagctgaa aca                                               23

<210> SEQ ID NO 6
<211> LENGTH: 23
<212> TYPE: DNA
<213> ORGANISM: Artificial Sequence
<220> FEATURE:
<223> OTHER INFORMATION: CD133-R6

<400> SEQUENCE: 6
tccgcaacat agccacacag aat                                               23

<210> SEQ ID NO 7
<211> LENGTH: 18
<212> TYPE: DNA

```
<213> ORGANISM: Artificial Sequence
<220> FEATURE:
<223> OTHER INFORMATION: GFAP-F7

<400> SEQUENCE: 7
gaggcagaag ctccaaga                                                   18

<210> SEQ ID NO 8
<211> LENGTH: 20
<212> TYPE: DNA
<213> ORGANISM: Artificial Sequence
<220> FEATURE:
<223> OTHER INFORMATION: GFAP-R8

<400> SEQUENCE: 8
gctctaggga ctcgttcgtg                                                 20

<210> SEQ ID NO 9
<211> LENGTH: 20
<212> TYPE: DNA
<213> ORGANISM: Artificial Sequence
<220> FEATURE:
<223> OTHER INFORMATION: GalC-F9

<400> SEQUENCE: 9
ccactggacc aacatgactg                                                 20

<210> SEQ ID NO 10
<211> LENGTH: 20
<212> TYPE: DNA
<213> ORGANISM: Artificial Sequence
<220> FEATURE:
<223> OTHER INFORMATION: GalC-R10

<400> SEQUENCE: 10
gccctgaacc aaaatcaaaa                                                 20

<210> SEQ ID NO 11
<211> LENGTH: 20
<212> TYPE: DNA
<213> ORGANISM: Artificial Sequence
<220> FEATURE:
<223> OTHER INFORMATION: MAP2-F11

<400> SEQUENCE: 11
ggatgggctt gtgtctgatt                                                 20

<210> SEQ ID NO 12
<211> LENGTH: 20
<212> TYPE: DNA
<213> ORGANISM: Artificial Sequence
<220> FEATURE:
<223> OTHER INFORMATION: MAP2-R12

<400> SEQUENCE: 12
ctggacccac tccacaaact                                                 20

<210> SEQ ID NO 13
<211> LENGTH: 20
<212> TYPE: DNA
<213> ORGANISM: Artificial Sequence
<220> FEATURE:
<223> OTHER INFORMATION: NFH-F13

<400> SEQUENCE: 13
cagctggaca gtgagctgag                                                 20
```

```
<210> SEQ ID NO 14
<211> LENGTH: 20
<212> TYPE: DNA
<213> ORGANISM: Artificial Sequence
<220> FEATURE:
<223> OTHER INFORMATION: NFH-R14

<400> SEQUENCE: 14
ggcctcttct ttcacacgag                                               20

<210> SEQ ID NO 15
<211> LENGTH: 20
<212> TYPE: DNA
<213> ORGANISM: Artificial Sequence
<220> FEATURE:
<223> OTHER INFORMATION: GAPDH-F15

<400> SEQUENCE: 15
aactttggca ttgtggaagg                                               20

<210> SEQ ID NO 16
<211> LENGTH: 20
<212> TYPE: DNA
<213> ORGANISM: Artificial Sequence
<220> FEATURE:
<223> OTHER INFORMATION: GAPDH-R16

<400> SEQUENCE: 16
ccctgttgct gtagccgtat                                               20
```

ULTRA-NANOCRYSTALLINE DIAMOND AS A BIOMATERIAL FOR ENHANCING PROLIFERATION AND DIFFERENTIATION OF NEURAL STEM CELLS

FIELD OF THE INVENTION

The present invention relates generally to the supporting surface for stem cell growth, and more specifically to biomaterials for promoting neural stem cell growth and differentiation.

BACKGROUND OF THE INVENTION

Special patented devices containing silicon-based microelectrode arrays have been inserted into the cortex of patients in order to cure spinal cord injury, and the devices have been shown to stimulate a stable population of cortical neurons on a long-term basis. Similar devices might be ultimately used in a wide range of injuries to the central nervous system. However, these widely used silicon-based devices can easily generate debris particles, and when devices are implanted into human bodies, these debris could cause local damage and inflammation. Therefore, it is desirable to explore other biomaterials with better mechanical, thermal, chemical and tribological properties that may be suitable to replace the silicon-based devices generally used in biomedical applications.

Ultra-nanocrystalline diamond (UNCD) films with grains of 2-5 nm and a smooth surface of 10-20 nm root-mean-square (RMS) are candidates for use in the fabrication of multifunctional devices, such as for microelectromechanical systems (MEMS) that require a high Young's modulus, low friction coefficient and high resistance to wear. UNCD films could also be used in biomedical devices requiring bioinertness and non-cytotoxicity. Combining these superior characteristics, UNCD is a potential material for use in biomedical devices such as bioMEMS. Diamond coatings have the chemical inertness and impermeability required to reduce the crevice corrosion that is commonly seen in conventional metallic implants. Recently, the suitability and noncytotoxicity of ultra-nanodiamond films as a support surface for cell growth and proliferation has been proven. Moreover, Xiao et al. demonstrated the successful insertion of UNCD bioinert encapsulation coatings of silicon microchips into human eyes. Responses of neural stem cells (NSCs) to nanoscale surface features and different electron affinities resulted from surface modification of UNCD films have not been studied.

A heretofore unaddressed need exists in the art to address the aforementioned deficiencies and inadequacies, especially in connection with the method of identifying drug candidates for treating cancer, inflammatory diseases, and/or angiogenesis-associated diseases.

SUMMARY OF THE INVENTION

In one aspect, the invention relates to a composition comprising: a) a diamond film; b) a stem cell cultured on the diamond film; and c) a medium bathing the stem cell.

In another aspect, the invention relates to a composition comprising: a) a diamond film, comprising a hydrogen-terminated or an oxygen-terminated surface; b) a neural stem cell cultured on the hydrogen-terminated or oxygen-terminated surface of the diamond film; and c) a medium bathing the neural stem cell. The composition may further comprise a neuronal cell and/or an oligodendrocyte differentiated from the neural stem cell, in which the medium is free of a differentiation agent. Alternatively, the composition may further comprise a neuronal cell differentiated from the neural stem cell, in which the medium is free of a differentiation agent and the neural stem cell is cultured on the hydrogen-terminated surface of the diamond film.

In another aspect, the invention relates to an implant material comprising one of the aforementioned compositions.

Further in another aspect, the invention relates to a method for promoting growth and/or differentiation of a stem cell. The method comprises the steps of:
a) providing a composition comprising:
  i) a diamond film;
  ii) a stem cell cultured on the diamond film; and
  iii) a medium bathing the stem cell;
  wherein the diamond film comprises either a hydrogen-terminated or oxygen-terminated surface; and
b) culturing the stem cell on the diamond film with the medium for a period and thereby promoting the growth and/or differentiation of the stem cell.

Further in another aspect, the invention relates to a method for promoting growth and/or differentiation of a stem cell. The method comprises the steps of:
a) providing a composition comprising:
  i) a diamond film comprising a hydrogen-terminated or an oxygen-terminated surface;
  ii) a neural stem cell cultured on the hydrogen-terminated or oxygen-terminated surface of the diamond film; and
  iii) a medium bathing the neural stem cell; and
b) culturing the stem cell on the diamond film with the medium for a period and thereby promoting the growth and/or differentiation of the stem cell.

In one embodiment of the invention, the diamond film in the composition is an ultra-nanocrystalline diamond (UNCD) film. The diamond film may be deposited or coated onto the surface of a substrate.

In another embodiment of the invention, the stem cell in the composition is an embryonic stem cell.

In another embodiment of the invention, the stem cell in the composition is a mammalian neural stem cell.

In another embodiment of the invention, the composition further comprises a neurosphere derived from the neural stem cell, in which the diamond film comprises a hydrogen-terminated surface.

In another embodiment of the invention, the composition further comprises a neural stem cell-differentiated cell.

In another embodiment of the invention, the neural stem cell-differentiated cell is a neuronal cell phenotype or an oligodendrocyte cell phenotype.

In another embodiment of the invention, the medium is free of a differentiation agent.

Further in another embodiment of the invention, the medium comprises no more than 2% of bovine serum.

Yet in another embodiment of the invention, the diamond film comprises a hydrogen-terminated or an oxygen-terminated surface.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIGS. 4a-4f are micrographs of immunofluorescence-stained cells grown on polystyrene coated with poly-D-lysine (PS), H-UNCD (H), or O-UNCD (O), showing the effects of substrates on neuronal differentiation of NSCs. The differentiated cells were verified using neuron-specific anti-TuJ1 antibody conjugated with rhodamine (Red) and anti-GFAP antibody conjugated with fluorescein (Green). In the basal medium supplemented with 2% FBS only (FBS), some of the TuJ1-positive cells grown on (a) PS, (b) H-UNCD, and (c) O-UNCD are indicated by arrows. After treatment with specific neuronal differentiation reagents (FBS+PBG), the TuJ1-positive cells grown on (d) PS, (e) H-UNCD, and (f) O-UNCD are also indicated by arrows. Scale bars represent 200 mm. The magnification is 200×. The TuJ1-positive cells marked by arrowheads are enlarged in the insets.

FIGS. 5a-5f are micrographs of immunofluorescence-stained cells grown on polystyrene coated with poly-D-lysine (PS), H-UNCD (H), and O-UNCD (O), showing the effects of substrates on oligodendrocyte differentiation of NSCs. The differentiated cells were stained with oligodendrocyte-specific anti-GalC antibody conjugated with rhodamine (Red) and anti-GFAP antibody conjugated with fluorescein (Green). In the basal medium supplemented with 2% FBS (FBS), some of the GalC-positive cells grown on (a) PS, (b) H-UNCD, and (c) O-UNCD are indicated by arrows. Where the oligodendrocyte induction was conducted by treating NSCs with the thyroid hormone neuronal 3',3,5-Triiodothyronine (T3) (FBS+T3), the GalC-positive cells grown on (d) PS, (e) H-UNCD, and (f) O-UNCD are also indicated by arrows. Scale bars represent 200 mm. The magnification is 200×.

DETAILED DESCRIPTION OF THE INVENTION

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate; meaning that the term "around", "about" or "approximately" can be inferred if not expressly stated.

As used herein, the term "implant" shall generally mean any device or material, esp. of an inserted substance, used for repairing or replacing part of the body.

As used herein, the term "nanocrystalline diamond" shall generally means a diamond film whose crystalline morphology disappears but it still possess many of the desirable properties of diamond while being much smoother. A nanocrystalline diamond may be considered to be an aggregate of diamond nanocrystals.

OVERVIEW OF THE INVENTION

Clinical applications of NSCs in vivo require precise controlling of differentiation because most injuries to the central nervous system are caused by the loss or damage of a specific sub-population of the neural lineages. The focus of the invention is on obtaining neuronal and oligodendrocyte phenotype differentiation from NSCs because of the central role of neurons and the supporting role of oligodendrocytes in the nervous system. We discovered that the differentiation potential of NSCs was enhanced when cultured on UNCD films modified by hydrogen (H—) or oxygen (O—) surface treatment. We describe the nature of the exposed surfaces of modified UNCD films and polystyrene, and compared the cellular responses of NSCs to H- and O-terminated UNCD with those to polystyrene. The inventors discovered that H-terminated UNCD films supported NSC differentiation into neurons, while the O-terminated UNCD films favored NSC differentiation into oligodendrocytes (Chen et al., (2009) "The effect of ultra-nanocrystalline diamond films on the proliferation and differentiation of neural stem cells" *Biomaterials* 30 3428-3435, which is herein incorporated by reference in its entirety).

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods

Preparation of Ultra-Nanoctystalline Diamond Films

Ultra-nanoctystalline diamond (UNCD) films were prepared by microwave plasma chemical vapor deposition (MPCVD) in a 6" CYRANNUS I IPLAS (Innovative Plasma Systems GmbH), using $Ar/CH_4$ (99% Ar/1% CH4) as a reactant gas. The films were grown for 1 h on quartz dishes into slices of 2.5 cm and 1 cm in diameter. Prior to the deposition of the UNCD films by the MPCVD process, the substrates were ultrasonicated in the methanol solution containing nanodiamond and titanium powders for 30 min in order to create the nucleation sites necessary for growing the UNCD films.

Surface Modification of UNCD

After deposition of the UNCD films, the surface atoms were passivated with either H or O atoms by post-treatment with pure hydrogen or oxygen plasmas at 5 Torr with a microwave power of 600 W, resulting in H-terminated UNCD (H-UNCD) or O-terminated UNCD (O-UNCD) films. The surface bonding states were characterized by X-ray photoelectron spectroscopy (XPS).

Surface Analysis Using HRTEM, AFM, XPS and Contact Angle Measurement

The characteristics of the UNCD films were characterized with high-resolution transmission electron microscopy (HRTEM, Gatan JEM-2100F) at 200 keV and nearedge X-ray absorption fine structure (NEXAFS) at the National Synchrotron Radiation Research Center, Taiwan.

Surface roughness was examined with atomic force microscopy (AFM, Vecco D3100) using the tapping mode operated at room temperature. A scanning area of 5×5 μm was studied. The surface root-mean-square (RMS) roughness was calculated as $\Sigma(Z_i-Z_{av})/N$, where $Z_i$ is the individual height, N is the number of pixels, and $Z_{av}$ is the average of the Z height in a given area.

The surface bonding states of the H-UNCD and O-UNCD films and polystyrene dishes were examined using X-ray photoelectron spectroscopy (XPS) (PHI, 1600) at room temperature in an ultra-high vacuum (pressure $<10^{-9}$ Torr). The hydrophilicity of the surface was evaluated according to the sessile drop method by measuring the water contact angles at three different points for each sample.

Cell Culture

Neural stem cells (NSCs) were isolated and cultured according to a method described previously. Mouse embryos at day 11.5 were collected from pregnant FVB mice (n=3) and placed in a basal medium (a 1:1 mixture of Dulbecco's modified Eagle's medium high glucose and Ham's F12 medium (Gibco) containing 100 units/ml penicillin and 100 μg/ml streptomycin). The brain tissue was removed from the embryos under a dissection microscope (MZ6 Leica) and enzymatically dissociated in 1 mg/ml of hyaluronidase and collagenase (Sigma-Aldrich) at 37° C. for 10 min. Basal medium ten times the volume of the enzymatic digestion was added to the preparation. The diluted material was centrifuged at 800×g for 5 min to collect the cell/tissue pellet. The cell/tissue pellet was digested with 0.05% (wt/vol) trypsin-0.53 mM EDTA (Gibco) at 37° C. for 5 min. Basal medium ten times the volume of enzymatic solution was added to neutralize trypsin. The diluted preparation was centrifuged at 800×g for 5 min to collect the cell pellet. The pellet was resuspended by triturating mechanically to yield a single cell suspension. The cells were filtered through a sterile nylon mesh (40 mm; BD Science) and washed with basal medium. The neural stem/progenitor cells were cultured on polystyrene Petri dishes (Falcon) in a humidified 5% $CO_2$ incubator at 37° C. The culture medium of NSCs contained DMEM/F12 (Gibco), $1 \times N_2$ (Gibco), 20 ng/ml EGF (R&D Systems), 20 ng/ml FGF2 (R&D Systems) and 5 μg/ml heparin (Sigma). At 7 days in culture, the cells were collected and mechanically dispersed into single cells by triturating and passaged. The single cells were seeded onto polystyrene Petri dishes (Falcon), H-UNCD- and O-UNCD-coated dishes, respectively, at a density of $1 \times 10^5$ cells/ml in the culture medium for 4 days. The cells were then collected for sequence analysis.

For the cell proliferation assay, cells were seeded onto polystyrene dishes, HUNCD and O-UNCD coated dishes, respectively, at a density of $1.5 \times 10^4$ cells/cm². At days 4 and 7 after seeding, cells were stained with trypan blue and counted with a hematocytometer.

Neurosphere Formation, Neurogenesis and Immunofluorescence Staining

For neurosphere formation, cells were washed with basal medium and seeded at a maximum density of $1 \pm 10^3$ cells/ml onto a 60-mm Petri dish in 7 ml of the neurosphere medium containing basal medium supplemented with B27 (Gibco), 20 ng/ml EGF (R&D Systems), 20 ng/ml FGF2 (R&D Systems), and 2 μg/ml heparin (Sigma). The cells were cultured in a humidified 5% $CO_2$ incubator at 37° C. without shaking for 10 days. The spheres (about 75-100 μm in diameter) were counted under a microscope and the efficiency of neurosphere formation was estimated to be about 0.43%. Occasionally, larger neuronspheres of about 100-200 μm (<10%) were also observed. In extremely rare cases, spheres of about 200-300 µm were formed due to aggregation. This aggregation could be avoided if cells were not moved during the 10 day-incubation period.

To evaluate the capacity of neural differentiation, the neurospheres were dissociated into single cells using a 0.05% trypsin-0.53 mM EDTA solution, and the single cells were cultured in a basal medium supplemented with 2% fetal bovine serum (FBS) with or without specific differentiating reagents. The cells were seeded onto HUNCD films, O-UNCD films and poly-D-lysine-coated polystyrene plates (BD Bioscience) in a basal medium supplemented with 2% FBS for 24 h, and then switched to a specific neural cell differentiating medium. For neuronal differentiation, the medium (PBG) contained 10 ng/ml of recombinant human platelet-derived growth factor-BB (PDGF-BB; R&D Systems), 50 ng/ml recombinant human brain-derived neurotrophic factor (BDGF; R&D Systems), and 50 ng/ml recombinant human glial cell line-derived neurotrophic factor (GDNF; R&D). For oligodendroglial differentiation, 1 µM/ml T3 (Sigma-Aldrich) was used. After 7-9 days, the differentiation capacity was assayed by immunofluorescence staining.

The cells on slides were fixed with 4% paraformaldehyde for 20 min at room temperature, and washed with phosphate-buffered saline (PBS) containing 0.1% Tween-20. Cells were treated with 1% FBS in PBS for 1 h at room temperature before being incubated at 4° C. overnight with a mouse monoclonal antibody to neuron specific βIII tubulin (TuJ1, 1:400; Abcam), rabbit polyclonal to glial fibrillary acidic protein (GFAP, 1:600; Abcam), and a mouse monoclonal antibody to galactocerebroside (GalC, 1:500; Chemicon). The cells were then incubated with the appropriate FITC- or rhodamine-conjugated secondary antibodies, diluted 1:1000, for 1 h at room temperature. The cell nuclei were stained with Hoechst 33258, and at least 10 images of each staining condition were captured at a 200× magnification. Three thousand cells were manually counted to obtain the positive-stained fractions (DAPI staining was used as counter staining).

Reverse Transcription Polymerase Chain Reaction

To further characterize cell phenotypes, reverse transcription polymerase chain reaction (RT-PCR) assays were performed on known the NSC markers CD133 and Sox2, the neuronal progenitor cell marker Sox1, and the astroglia lineage marker anti-glial fibrillary acidic protein (GFAP). Total RNA was extracted from the cultured cells with an RNeasy Mini Kit (QIAGEN), and an aliquot of 1 µg RNA was reverse transcribed into cDNA by using RevertAid™ H Minus M-MuLV Reverse Transcriptase (Ferments) with a poly-dT primer according to the manufacturer's instructions. Polymerase chain reaction analyses were performed with gene-specific primers (Table 1) using a PCR Master Mix kit (GeneMark) according to the manufacturer's instructions. Table 1 lists the primer sequences used for RT-PCR analyses.

Statistics

All data were represented as the mean±standard deviation of at least 3 independent experiments. Statistical analysis was performed using a one-way analysis of variance (ANOVA) test followed by the least significant difference test (LST) to evaluate the statistical significance between the different materials. The significance levels were set at *$p<0.05$, $p<0.01$, and *$p<0.001$.

TABLE 1

| | Sequence of forward primer | SEQ ID NO. | Sequence of reverse primer | SEQ ID NO. |
|---|---|---|---|---|
| Sox2 | agaaccccaagatgcacaa | 1 | atgtaggtctgcgagctggt | 2 |
| Sox1 | cacagcactaccagggcgcg | 3 | cacctctgagaggggatt | 4 |
| CD133 | ttgcctgaaggaaagctgaaaca | 5 | tccgcaacatagccacacagaat | 6 |
| GFAP | gaggcagaagctccaaga | 7 | gctctagggactcgttcgtg | 8 |
| GalC | ccactggaccaacatgactg | 9 | gccctgaaccaaaatcaaaa | 10 |
| MAP2 | ggatgggcttgtgtctgatt | 11 | ctggacccactccacaaact | 12 |
| NFH | cagctggacagtgagctgag | 13 | ggcctcttctttcacacgag | 14 |
| GAPDH | aactttggcattgtggaagg | 15 | ccctgttgctgtagccgtat | 16 |

Results

Characterization of Ultra-Nanocrystalline Diamond Films

Figure 1:
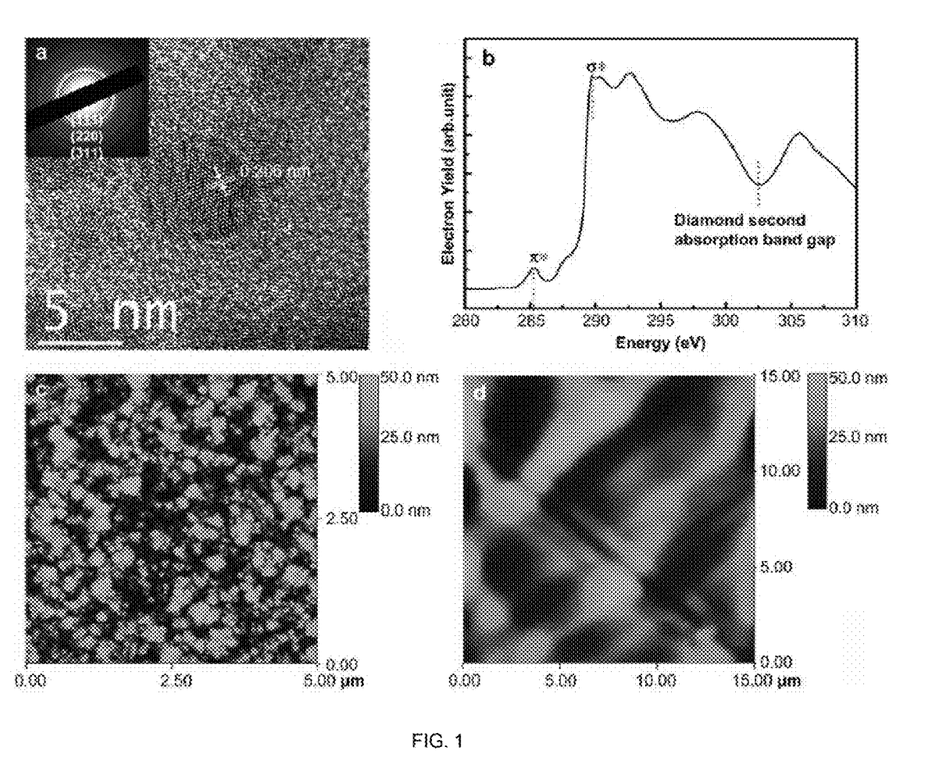
FIG. 1a is an HRTEM image of a UNCD film showing a diamond grain of around 5 nm with a d spacing of 0.206 nm. The top left inset shows the selected area electron diffraction (SAED) pattern, which can be indexed as polycrystalline diamond.
FIG. 1b is a NEXAFS spectrum of the top surface of a UNCD film, showing a very low fraction of sp2-bonded carbon in the UNCD film.
FIG. 1c is an atomic force microscope (AFM) image of a UNCD film grown for 1 h, showing a surface roughness of 16.3 nm RMS.
FIG. 1d is an AFM image of a polystyrene Petri dish (control), showing a surface roughness of 11.6 nm RMS.

The HRTEM image of the ultra-nanocrystalline diamond (UNCD) film (FIG. 1a) showed the structure of a diamond grain of about 5 nm in size. The selected area electron diffraction pattern (SAED), inset of FIG. 1a, showed diffraction rings corresponding to the {111}, {220} and {311} planes of diamond. These images clearly indicated the sp3-bonded nature and randomly oriented characteristics of the UNCD grains. To unambiguously distinguish the sp3-bonded from the sp2-bonded carbon in the carbon materials, NEXAFS was performed. FIG. 1b shows the C(1s) NEXAFS spectra of the UNCD films, revealing two typical characteristics of diamond: a sharp peak at 289.3 eV corresponding to the C 1s-σ* C—C transition, and a dip at 302 eV corresponding to the second absorption band gap of diamond. A small peak at 285 eV corresponding to the C1s-π* transition indicated the presence of the sp2-bonded carbon, presumably located along the grain boundaries of the UNCD film. FIGS. 1c and d shows the topology of the UNCD film and polystyrene Petri dish, indicating that the surface roughness (RMS) was 16.3 nm and 11.6 nm over a 5×5 µm and 15×15 µm scanning area, respectively. The HRTEM, NEXAFS and AFM analyses demonstrated that the UNCD films exhibited uniform, nanosized crystalline diamond grains with low non-diamond phase content and a very smooth surface throughout the film, which are marvelous characteristics for biomedical applications.

Surface Characterization of H-UNCD, O-UNCD and Polystyrene Petri Dish

Figure 2:
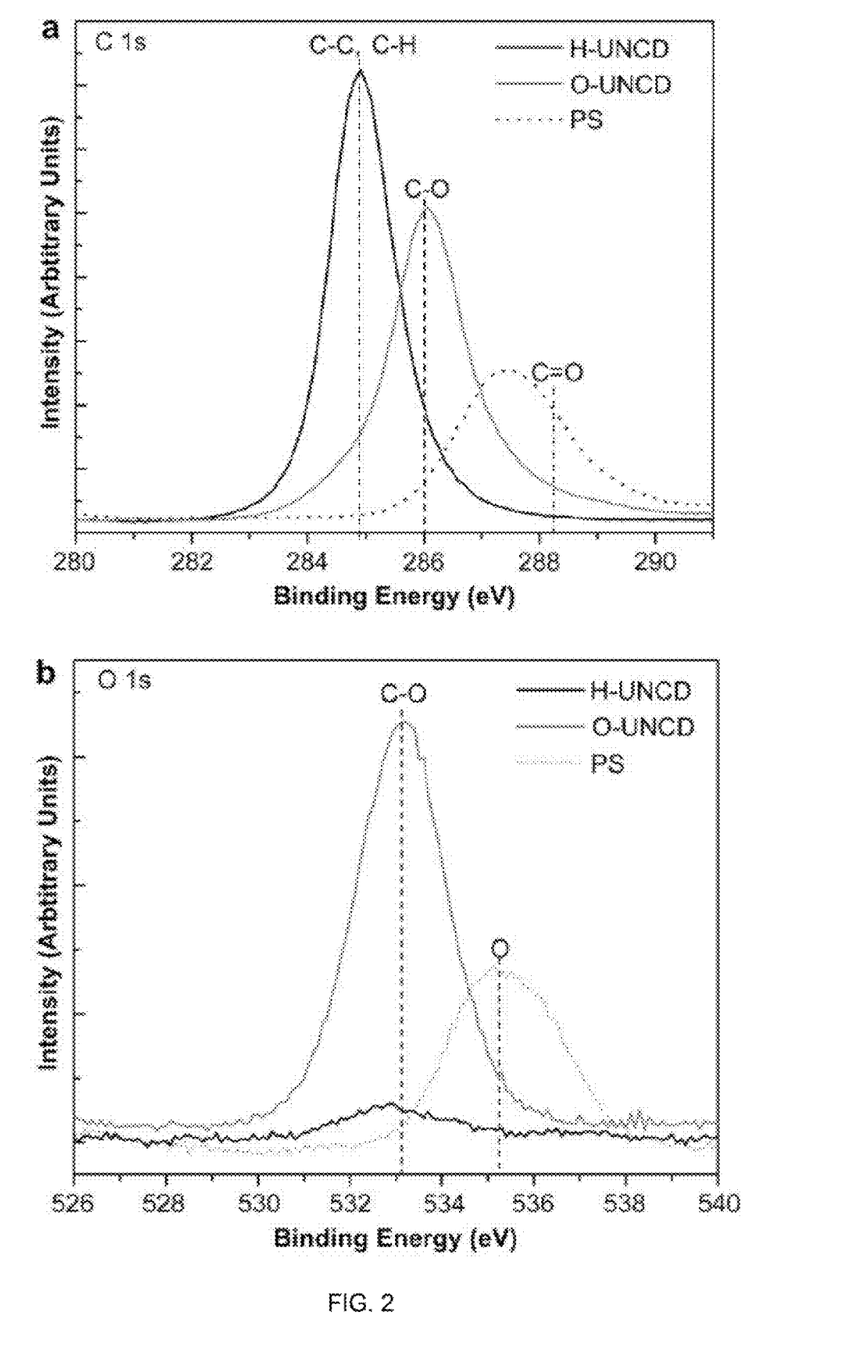
FIG. 2a is a graph of carbon 1 s (C 1s) X-ray photoelectron spectroscopy (XPS) spectra of H-terminated UNCD (H-UNCD), O-terminated UNCD (O-UNCD) and polystyrene (PS).
FIG. 2b is a graph of oxygen 1s (O 1s) XPS spectra of H-terminated UNCD (H-UNCD), O-terminated UNCD (O-UNCD) and polystyrene (PS).

The surface characteristics of the H-UNCD, O-UNCD and polystyrene were examined with XPS. FIG. 2 reveals that, for the HUNCD films, a high content of C—C and C—H bonds (~285 eV) and a low content of C—O bonds (~532.5 eV) were observed in C 1s (FIG. 2a) and O 1s (FIG. 2b), respectively. By contrast, the O-UNCD films showed a significantly higher number of C—O bonds in C 1s (~286 eV, FIG. 2a) and O 1s (~532.5 eV, FIG. 2b). Moreover, the surface of the commercial polystyrene consisted mainly of C—O, C=O bonds (FIG. 2a) and some adsorbates such as a thin water film observed at ~535 eV (FIG. 2b). Moreover, the water contact angle measurement indicated that the H-UNCD and polystyrene substrates were hydrophobic with very similar contact angles (~78°, whereas the O-UNCD substrate was hydrophilic (contact angle ~20°).

Characterization of Neural Stem Cells on UNCD and Polystyrene

Figure 3:
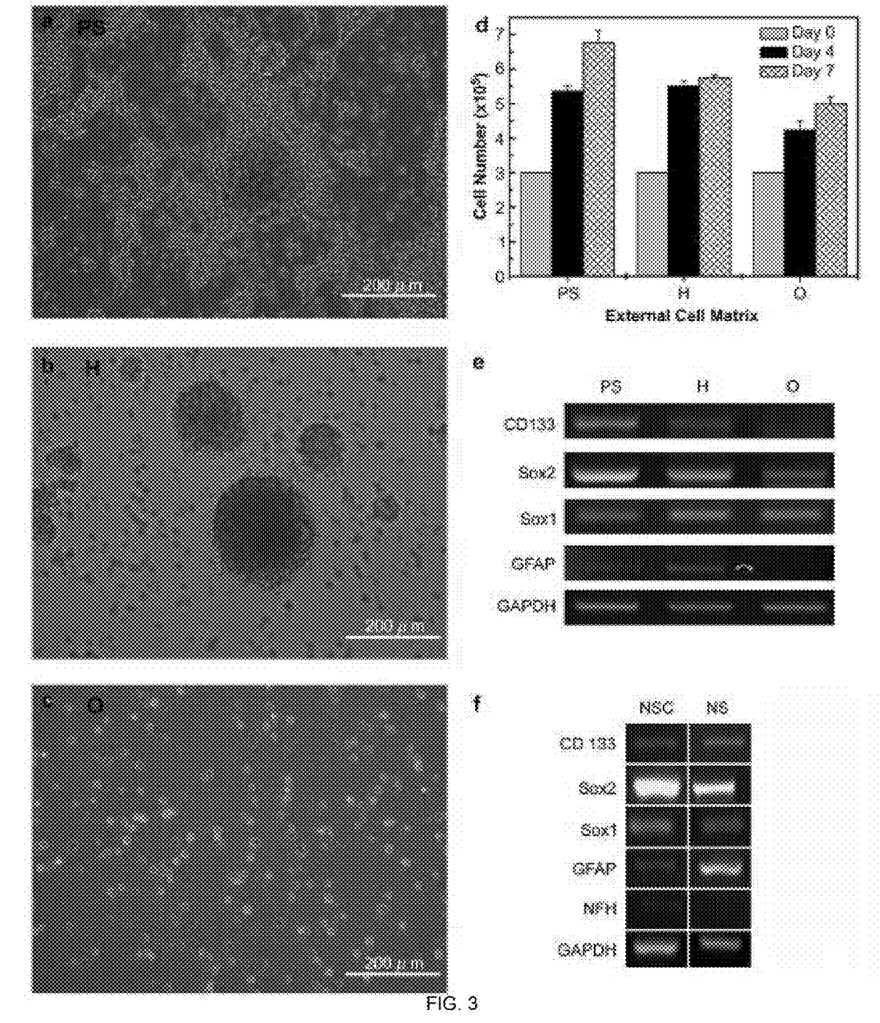
FIGS. 3a-3c are phase contrast light microscopy images showing the morphology of neural stem cells (NSCs) cultured in a serum-free medium for 4 days on a (a) polystyrene Petri dishes (PS), (b) H-UNCD film (H), and (c) O-UNCD film (O).
FIG. 3d is a graph showing results of cell proliferation assays of NSCs grown on the polystyrene Petri dish (PS), H-UNCD film (H), and O-UNCD film (O). Cells were counted after staining with trypan blue at 0, 4 and 7 days in culture. The error bars represent the standard deviation of the mean (n=3).
FIG. 3e is a photograph of gel electrophoresis of RT-PCR products, showing the expression of CD133, Sox2, Sox1, and GFAP genes. Cells grown on H- or O-UNCD films had lower expression levels of CD133 and Sox2 genes, but a higher expression level of Sox1 gene than those grown on PS.
FIG. 3f is a photograph of gel electrophoresis of RT-PCR products, showing both NSCs and neurospheres (NS) had similar expression of CD133, Sox2, and Sox1 genes.

The majority of cells grown on polystyrene dishes had high expression levels of CD133 and Sox2 genes, which confirmed their stem cell characteristics as NSCs. As reported in the previous studies, extracellular matrix (ECM) can regulate the proliferation and differentiation of NSCs. The present invention addresses the questions of the suitability of H-UNCD and O-UNCD films in culturing NSCs. The NSCs cultured on the H-UNCD films showed non-adherent sphere-formation cells. No any adherent cells were observed after 4 days in the culture (FIG. 3b). In contrast, neither non-adherent, sphere-forming cells nor adherent cells were detected when cells were grown on O-UNCD films (FIG. 3c). To assess the proliferation of the cells grown on the UNCD films, the cells were cultured and their numbers were counted after staining with trypan blue. The results showed that the cells proliferated well on either H-UNCD or O-UNCD films. Moreover, the cells grown on the H-UNCD films proliferated slightly better than those on the O-UNCD films (FIG. 3d). In addition, RT-PCR showed that the cells grown on both H- and O-UNCD films had lower levels of CD 133 and Sox2 gene expression, but had a higher level of Sox1 gene expression (FIG. 3d). These results demonstrated that the UNCD films could not only support the cell growth, but also regulated the cell fate of neural stem cell populations. Therefore, whether UNCD films possess high potential in neural differentiation was further explored.

Neural Differentiation of NSCs on H-UNCD, O-UNCD and Polystyrene

Neurosphere formation is still considered a gold standard for NSC identification and neural differentiation. The effects of the substrates were evaluated based on the immunofluorescence staining and RT-PCR results. Neuronspheres were cultured from NSCs for 10 days. The efficiency of neuronsphere formation was about 0.43%. The gene expression patterns of both NSCs and neuronspheres showed that the neural stem cell markers included CD133, Sox2, and Sox1 (FIG. 3f). GFAP was expressed in both populations, but the neuronal neurofilament H (NFH) marker was not detected (FIG. 3f). After differentiation for 7 days, the differentiation capacity was verified using immunofluorescence staining and RT-PCR. In the basal medium supplemented with 2% FBS only, the percentages of TuJ1-positive cells on polystyrene, H-UNCD and O-UNCD films were 3.0±1.1%, 13.2±0.9%, and 10.6±1.3%, respectively (FIGS. 4a-4c arrows, 4 g), and that of GalC-positive cells were 3.8±0.2%, 25.9±1.2%, and 32.1±1.9%, respectively (FIGS. 5a-c arrows, and 5g). The TuJ1-positive and GalC-positive cells exhibited the morphology of neurons and oligodendrocytes, respectively. After treatment with specific neuronal differentiation agents, the percentages of TuJ1-positive cells on polystyrene, HUNCD and O-UNCD films were 6.4±1.2%, 14.8±1.3%, and 17.2±1.0%, respectively (FIGS. 4d-f arrows, and 4g).

Figure 4:
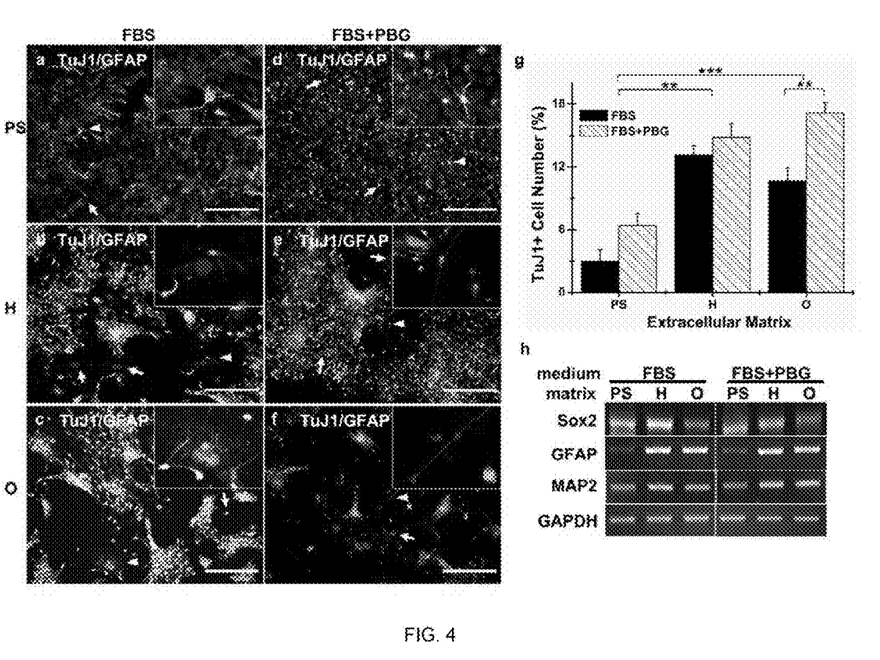
FIG. 4g is a graph showing the percentage of TuJ1-positive cells grown under different culture conditions. All values are expressed as means±standard deviation of the mean (n=3, more than 3000 cells were counted for each sample). Significance level: **p<0.01.
FIG. 4h is a photograph of an electrophoresis gel of RT-PCR products showing specific expression of genes in the NSCs of FIG. 4g.

The differentiated cells grown on the H-UNCD and O-UNCD films exhibited a higher percentage of TuJ1-positive neuronal cells than did those grown on polystyrene (FIG. 4g, p<0.01). This difference could be observed regardless whether the differentiating reagents were present in the culture medium. Furthermore, on the O-UNCD film the percentage of TuJ1-positive cells further increased after the addition of the differentiating reagent. There was no significant difference between the H- and O-UNCD films as to whether the NSCs were grown in the neuronal differentiation medium (FIG. 4g). The expression of the neuron-specific marker, microtubule-associated protein 2 (MAP2), was also verified with the RT-PCR assay. Cells collected from the HUNCD- or O-UNCD-film-coated dishes exhibited stronger signals than did those collected from the polystyrene dishes (FIG. 4h). The data indicated that the UNCD films, particularly the H-UNCD films, could be used for neuronal differentiation.

The NSCs grown on the O-UNCD films in basal medium with 2% FBS, differentiated more efficiently into oligodendrocytes than did those grown on polystyrene or the H-UNCD films (FIG. 5g, p<0.001 and p<0.05, respectively). When oligodendrocyte induction was performed with thyroid hormone (T3) treatment, the percentage of the GalC-positive oligodendrocytes on the H-UNCD film (34.3±2.5%) was higher than on polystyrene (5.0±1.6%) or the O-UNCD film (24.2±0.9%) (FIG. 5d-g, p<0.001 and p<0.05, respectively). The nature of the oligodendrocytes was examined by staining with GalC antibody (FIG. 5d-e). The gene expression was also verified using RT-PCR. In the T3-free medium, differentiated cells grown on the H-UNCD and O-UNCD films exhibited stronger expression of GalC and GFAP than did those grown on polystyrene. After the treatment with T3, cells grown on the H-UNCD film had a higher level of GalC gene expression but a lower level of GFAP gene expression than did those grown on the O-UNCD films. The RT-PCR results were consistent with those from immunostaining with GalC-specific antibody, which indicated that the cells grown on the O-UNCD films favored oligodendrocyte differentiation more than those grown on the H-UNCD films. After T3 was added into the medium, there was not a significant increase in the GalC-positive cells on polystyrene or UNCD film (FIG. 5g, gray vs. hatched boxes). Interestingly, the T3-treated cells showed a significant extension and complexity of the dendrites.

DISCUSSION

The interaction of ultra-nanocrystalline diamond (UNCD) with neural stem cells (NSCs) has been studied along with its surface modification in order to improve its function as a biomaterial. Hydrogen- and oxygen-terminated UNCD films were compared with standard grade polystyrene in terms of their impact on the growth, expansion and differentiation of NSCs. When NSCs were cultured on these substrates in low serum and without any differentiating factors, the hydrogen-terminated UNCD films spontaneously induced cell proliferation and neuronal differentiation. The oxygen-terminated UNCD films also improved differentiation, with a preference toward differentiation into oligodendrocytes. Hence, controlling the surface properties of the UNCD film could manipulate the differentiation of NSCs for various biomedical applications. These observations raised the potential for the use of the UNCD as a biomaterial for central nervous system transplantation and tissue engineering.

The extracellular matrix (ECM) environment of the central nervous system is responsible for a large number of regulatory functions during the development and the adulthood.

Previous studies have shown that the interaction between stem cells and different ECMs is critical for the cell growth, differentiation and migration through signaling from the surrounding matrix. Therefore, the composition of ECM, especially the top surface, may play an important role in regulating the differentiation of NSCs.

Diamond films produced by the chemical vapor deposition technique have been shown to be an excellent non-cytotoxic material. The UNCD films are similar to the natural diamond, with high mechanical strength and exceptional chemical inertness. The purpose of this study was to evaluate in vitro responses of NSCs to UNCD films. It was discovered that NSCs exhibited high growth and differentiation potential on the UNCD films as compared with NSCs on polystyrene, which is a universal substrate used to grow tissue culture cells.

Earlier studies have shown that the nanodiamond surfaces provide a unique platform for bioconjugation with biomolecules such as DNA and proteins after surface modification, suggesting that diamond may be an ideal substrate for use in the integration of microelectronics with biological modification and sensing systems. Specht and Ruiz have demonstrated ordered growth of neurons on protein-coated diamond using the micro-patterning technique. Ariano and co-workers have shown neuronal cell excitability on functionalized diamond surfaces. The biological responses of stem cells to the functionalized ultra-nanocrystalline diamond surfaces have not been reported. Cellular adhesion is of fundamental importance in many biological processes because the adhered cells can sense, interpret, integrate, and respond to extracellular signals through specific interactions between their contact sites and cell surface receptors. The chemical and physical signals from the substrate, such as surface energy, topography, electrostatic charge, and hydrophilicity, play critical roles in the regulation of the biological activities of cells, e.g. proliferation, differentiation and migration.

NSCs can be cultured in a serum-free medium containing EGF and FGF2. Under this condition, one observes non-adherent sphere-forming cells and cells that adhere to polystyrene dishes. Importantly, in our study we observed only sphere-forming cells growing on H-UNCD. On O-UNCD films we did not observe any adherent or non-adherent spheres. These observations suggested that the UNCD film is a more favorable culture surface for use in neural differentiation.

Figure 5:
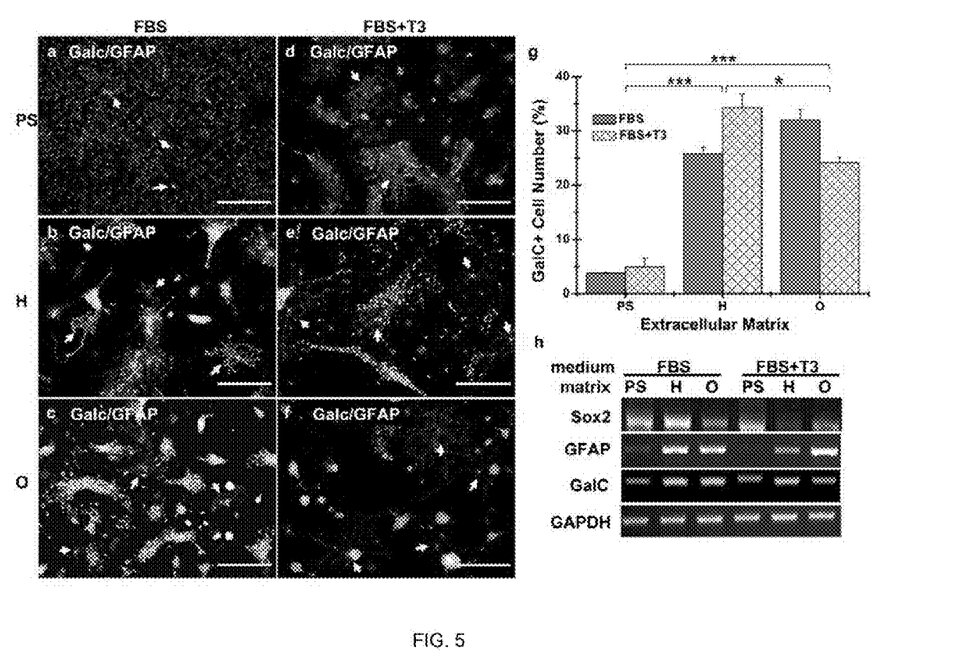
FIG. 5g is a graph showing the percentage of GalC-positive cells grown under different culture conditions. All values are expressed as means±standard deviation of the mean (n=3, more than 3000 cells were counted for each sample). Significance levels: *p<0.05, p<0.01 and *p<0.001.
FIG. 5h is a photograph of an electrophoresis gel of RT-PCR products showing specific expression of genes in the NSCs of FIG. 5g.

In comparison with the polystyrene dish as a control, it was discovered that in the absence of inducing factors such as growth factors, cytokines or hormones, the UNCD films exhibited a higher differentiation potential toward neurons and oligodendrocytes. In addition, the propensity toward neurons or oligodendrocytes depended on the different surface treatment. The H-UNCD films favored neuron differentiation, while the O-UNCD films favored oligodendrocyte differentiation. After adding platelet-derived growth factor (PDGF), Brain-derived growth factor (BDGF) and glial cell-derived neurotrophic factor (GDNF) for neuronal differentiation, there was an increase in the gene expression of microtubule-associated protein 2 (MAP2) in the cells grown on the H-UNCD and O-UNCD films as compared to those grown on polystyrene. This result was supported by a correspondingly high percentage of neuron-specific class III beta-tubulin (TuJ1)-positive cells grown on the H- and O-UNCD films (FIG. 5). There was no significant difference between the H- and O-UNCD films in terms of neuronal differentiation. In comparison with the H-UNCD films in terms of neural differentiation, cells grown on the O-UNCD films exhibited a preference toward oligodendrocyte differentiation. Previous studies have suggested that the bindings of growth factors to ECMs not only localize the growth factors to the immediate environment of the cells, but also specify their biological activities. The source of growth factors could be the 2% FBS in the medium or synthesized by the cells per se. Therefore, the enhancement of differentiation discovered here on the H- and O-UNCD films could be the concerted actions of specific interactions and competitions among the cell surface receptors, inherent growth factors, and the binding sites on the UNCD films. In other words, the termination and composition of the UNCD films influence the composition of the biological bioenvironment on the surface and thus influence the interaction of the adhering cells.

CONCLUSION

The invention related to the use of UNCD films for primary neural stem cell culture. The UNCD coatings have significant biological effects on NSCs. Both the H- and O-terminated UNCD coatings significantly promoted the efficiency of NSC expansion and differentiation as compared to the polystyrene control, even in a medium without the differentiation reagents. The H- or O-terminations on the UNCD surface possessed distinctly different neural differentiation abilities toward neurons and oligodendrocytes. The differentiation propensities could be exploited in different implants for the treatment of central nervous system injuries. Not only can this finding contribute to the development of artificial grafts to improve graft cell integration and central nervous system regeneration, but it can also improve NSC-based cell transplantation and tissue engineering for neural tissue repair and regeneration.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A composition comprising:
   (a) an ultra-nanocrystalline diamond film, comprising a hydrogen-terminated or an oxygen-terminated surface;
   (b) a neural stem cell cultured on the hydrogen-terminated or oxygen-terminated surface of the ultra-nanocrystalline diamond film; and
   (c) a medium bathing the neural stem cell.

2. The composition of claim 1 further comprising a neuronal cell and/or an oligodendrocyte differentiated from the neural stem cell, wherein the medium is free of a differentiation agent.

3. The composition of claim 1, further comprising a neuronal cell differentiated from the neural stem cell, wherein the medium is free of a differentiation agent and the neural stem cell is cultured on the hydrogen-terminated surface of the diamond film.

4. The composition of claim 3, wherein the ultra-nanocrystalline diamond film comprises the hydrogen-terminated surface.

5. The composition of claim 1, wherein the stem cell comprises an embryonic neural stem cell.

6. The composition of claim 1, wherein the stem cell comprises a mammalian neural stem cell.

7. The composition of claim 6, further comprising a neurosphere derived from the neural stem cell, wherein the ultra-nanocrystalline diamond film comprises the hydrogen-terminated surface.

8. The composition of claim 6, further comprising a cell differentiated from the neural stem cell.

9. The composition of claim 8, wherein the cell differentiated from the neural stem cell exhibits a neuronal cell phenotype or an oligodendrocyte cell phenotype.

10. The composition of claim 8, wherein the medium is free of a differentiation agent.

11. The composition of claim 1, wherein the ultra-nanocrystalline diamond film comprises the oxygen-terminated surface.

12. An implant material comprising a composition according to claim 1.

13. An implant material comprising a composition according to claim 8.

14. The implant material of claim 13, wherein the diamond film comprises the hydrogen-terminated surface.

15. The implant material of claim 12, wherein the stem cell is a mammalian neural stem cell.

16. A method for promoting growth and/or differentiation of a neural stem cell, comprising the steps of:
   (a) providing a composition according to claim 1; and
   (b) culturing the neural stem cell on the ultra-nanocrystalline diamond film with the medium for a period and thereby promoting the growth and/or differentiation of the neural stem cell.

17. The method claim 16, wherein the diamond film comprises the hydrogen-terminated surface.

18. The method of claim 16, wherein the medium is free of a differentiation agent.

19. The method claim 16, wherein the stem cell is a mammalian neural stem cell.

20. A method for promoting growth and/or differentiation of a neural stem cell, comprising the steps of:
   (a) providing a composition according to claim 1; and
   (b) culturing the neural stem cell on the diamond film with the medium for a period and thereby promoting the growth and/or differentiation of the neural stem cell, wherein the ultra-nanocrystalline diamond film comprises the hydrogen-terminated surface and the neural stem cell comprises an embryonic neural stem cell.

* * * * *